(12) United States Patent
Boni et al.

(10) Patent No.: US 7,544,369 B2
(45) Date of Patent: Jun. 9, 2009

(54) SUSTAINED RELEASE OF ANTIINFECTIVES

(75) Inventors: Lawrence T. Boni, Monmouth Junction, NJ (US); Brian S. Miller, Mercerville, NJ (US)

(73) Assignee: Transave, Inc., Monmouth Junction, NJ (US)

( * ) Notice: Subject to any disclaimer, the term of this patent is extended or adjusted under 35 U.S.C. 154(b) by 586 days.

(21) Appl. No.: 10/696,389

(22) Filed: Oct. 29, 2003

(65) Prior Publication Data
US 2004/0142026 A1 Jul. 22, 2004

Related U.S. Application Data

(60) Provisional application No. 60/421,923, filed on Oct. 29, 2002.

(51) Int. Cl.
*A61K 9/127* (2006.01)
(52) U.S. Cl. ...................................................... 424/450
(58) Field of Classification Search ................... 424/450
See application file for complete search history.

(56) References Cited

U.S. PATENT DOCUMENTS

| 4,372,949 A | 2/1983 | Kodama et al. |
| 4,394,448 A | 7/1983 | Szoka, Jr. et al. |
| 4,396,630 A | 8/1983 | Riedl et al. |
| 4,451,447 A | 5/1984 | Kaplan et al. |
| 4,693,999 A | 9/1987 | Axelsson et al. |
| 4,767,874 A | 8/1988 | Shima et al. |
| 4,895,452 A | 1/1990 | Yiournas et al. |
| 4,895,719 A | 1/1990 | Radhakrishnan et al. |
| 4,897,384 A | 1/1990 | Janoff et al. |
| 4,933,121 A | 6/1990 | Law et al. |
| 4,952,405 A | 8/1990 | Yau-Young |
| 4,975,282 A | 12/1990 | Cullis et al. |
| 4,981,692 A * | 1/1991 | Popescu et al. ............. 424/422 |
| 5,000,958 A | 3/1991 | Fountain et al. |
| 5,006,343 A | 4/1991 | Benson et al. |
| 5,023,087 A | 6/1991 | Yau-Young |
| 5,030,453 A | 7/1991 | Lenk et al. |
| 5,049,388 A | 9/1991 | Knight et al. |
| 5,049,389 A | 9/1991 | Radhakrishnan |
| 5,059,591 A | 10/1991 | Janoff et al. |
| 5,077,056 A | 12/1991 | Bally et al. |

(Continued)

FOREIGN PATENT DOCUMENTS

EP 0069307 A 1/1983

(Continued)

OTHER PUBLICATIONS

Deol et al in Biochimica et Biophysica Acta, 1334, pp. 161-172, (1997).*

(Continued)

*Primary Examiner*—Gollamudi S Kishore
(74) *Attorney, Agent, or Firm*—Foley Hoag LLP

(57) ABSTRACT

Provided, among other things, is a method of treating or ameliorating pulmonary infection in a cystic fibrosis patient comprising pulmonary administration of an effective amount of a liposomal/complexed antiinfective to the patient, wherein the (i) administrated amount is 50% or less of the comparative free drug amount, or (ii) the dosing is once a day or less, or (iii) both.

26 Claims, 4 Drawing Sheets

SPUTUM/BIOFILM of CF PATIENTS

U.S. PATENT DOCUMENTS

| | | | |
|---|---|---|---|
| 5,169,637 A | 12/1992 | Lenk et al. | |
| 5,178,876 A | 1/1993 | Khokhar et al. | |
| 5,211,955 A | 5/1993 | Legros et al. | |
| 5,264,618 A | 11/1993 | Felgner et al. | |
| 5,269,979 A | 12/1993 | Fountain | |
| 5,279,833 A | 1/1994 | Rose | |
| 5,320,906 A | 6/1994 | Eley et al. | |
| 5,334,761 A | 8/1994 | Gebeyehu et al. | |
| 5,409,704 A | 4/1995 | Bally et al. | |
| 5,459,127 A | 10/1995 | Felgner et al. | |
| 5,540,936 A * | 7/1996 | Coe et al. | 424/450 |
| 5,543,152 A | 8/1996 | Webb et al. | |
| 5,569,464 A | 10/1996 | Endo et al. | |
| 5,616,334 A | 4/1997 | Janoff et al. | |
| 5,641,662 A | 6/1997 | Debs | |
| 5,643,599 A | 7/1997 | Lee et al. | |
| 5,662,929 A * | 9/1997 | Lagace et al. | 424/450 |
| 5,665,383 A | 9/1997 | Grinstaff et al. | |
| 5,723,147 A | 3/1998 | Kim et al. | |
| 5,741,516 A | 4/1998 | Webb et al. | |
| 5,753,613 A | 5/1998 | Ansell et al. | |
| 5,756,120 A * | 5/1998 | Hersch et al. | 424/450 |
| 5,756,353 A | 5/1998 | Debs | |
| 5,759,571 A | 6/1998 | Hersch et al. | |
| 5,766,627 A | 6/1998 | Sankaram et al. | |
| 5,795,589 A | 8/1998 | Mayer et al. | |
| 5,820,848 A | 10/1998 | Boni et al. | |
| 5,843,473 A | 12/1998 | Woodle et al. | |
| 5,849,490 A | 12/1998 | Schonwetter et al. | |
| 5,875,776 A | 3/1999 | Vaghefi | |
| 5,945,122 A | 8/1999 | Abra et al. | |
| 6,045,828 A | 4/2000 | Bystrom et al. | |
| 6,051,251 A | 4/2000 | Zalipsky et al. | |
| 6,090,407 A | 7/2000 | Knight et al. | |
| 6,147,060 A | 11/2000 | Zasloff et al. | |
| 6,211,162 B1 * | 4/2001 | Dale et al. | 514/44 |
| 6,221,388 B1 | 4/2001 | Hersch et al. | |
| 6,352,996 B1 | 3/2002 | Cao et al. | |
| 6,419,901 B2 | 7/2002 | Placke et al. | |
| 6,440,393 B1 | 8/2002 | Waldrep et al. | |
| 6,451,784 B1 | 9/2002 | Placke et al. | |
| 6,497,901 B1 | 12/2002 | Royer | |
| 6,511,676 B1 | 1/2003 | Boulikas | |
| 6,599,912 B1 | 7/2003 | Au et al. | |
| 6,843,942 B2 | 1/2005 | Katinger et al. | |
| 2001/0006660 A1 | 7/2001 | Lagace et al. | |
| 2002/0187105 A1 | 12/2002 | Zou et al. | |
| 2003/0059375 A1 | 3/2003 | Perez-Soler et al. | |
| 2003/0118636 A1 * | 6/2003 | Friesen et al. | 424/450 |
| 2005/0019926 A1 * | 1/2005 | Gonda et al. | 435/455 |

FOREIGN PATENT DOCUMENTS

| | | | |
|---|---|---|---|
| GB | 2145107 A | | 3/1985 |
| WO | WO-86/06959 | | 12/1986 |
| WO | WO-91/16882 | | 11/1991 |
| WO | WO-93/12240 | | 6/1993 |
| WO | 94/12155 | * | 6/1994 |
| WO | WO-94/12156 | | 6/1994 |
| WO | WO-96/19199 | | 6/1996 |
| WO | WO-96/19972 | | 7/1996 |
| WO | WO-99/65466 | | 12/1999 |
| WO | WO-00/27359 | | 5/2000 |
| WO | WO-00/29103 | | 5/2000 |
| WO | WO-03/075889 | | 9/2003 |

OTHER PUBLICATIONS

International Search Report, PCT/US03/34240 mailed on Jul. 12, 2005.

Niven, Ralph et al., Nebulization of Liposomes. I. Effects of Lipid Composition, Report, pp. 1127-1133.

Katare, O.P., et al., Enhanced in vivo Performance of Liposomal Indomethacin Derived From Effervescent Granule Based Proliposomes, J. Microencapsulation, 1995, vol. 12, No. 5, pp. 487-493.

Petkowicz, Jozefa, et al., Hypoglycemic Effect of Liposome-Entrapped Insulin Administered by Various Routes into Normal Rats, Pol. J. Pharmacol. Pharm., 1989, 41, pp. 299-304.

Comis, "Carboplatin in the Treatment of Non-Small Cell Lung Cancer: a Review," Oncology, 1993 Nov.; 50 (2): 37-41. (Abstract).

A.Bargoni, R. Cavalli, G.P. Zara, A. Fundaro, O. Caputo, M.R. Gasco (2001) Transmucosal transport of tobramycin incorporated in solid lipid nanoparticles (SLN) after duodenal administration to rats. Part II—Tissue distribution. Pharmacological Research 43(5):497-502.

J. Lagace, M. Dubreuil, S. Montplaisir (1991) Liposome-encapsulated antibiotics: preparation, drug release and antimicrobial activity against *Pseudomona aeruginosa*. Journal Microencapsulation 8(1): 53-61.

L.S. Ramsammy, G.J. Kaloyanides (1988) The effect of gentamicin on the biophysical properties of phosphatidic acid liposomes is influenced by the O–C=O group of the lipid. Biochemistry 27:8249-8254.

C. Dees, R.D. Schultz (1990) The mechanism of enhanced intraphagocytic killing of bacteria by liposomes containing antibiotics. Veterinary Immunology and Immunopathology 24: 135-146.

C. Beaulac, S. Sachetelli, J. Lagace (1999) Aerolization of low phase transition temperature liposomal tobramycin as dry powder in an animal model of chronic pulmonary infection caused by *Pseudomonas aeruginosa*. Journal Drug Targeting 7(1): 33-41.

J.F. Marier, J.L. Brazier, J. Lavigne, M.P. Ducharme (2003) Liposomal tobramycin against pulmonary infections of *Pseudomonas aeruginosa*: a pharmacokinetic and efficacy study following single and multiple intratracheal administrations in rats. Journal Antimicrobial Chemotherapy 52: 247-252.

E.A. Poyner, H.O. Alpar, M.R.W. Brown (1993) Preparation, properties and the effects of free and liposomal tobramycin on siderophore production by *Pseudomonas aeruginosa*. Journal Antimicrobial Chemotherapy 34: 43-52.

A. Omri, M. Ravaoarinoro, M. Poisson (1995) Incorporation, release and in vitro antibacterial activity of liposomal aminoglycosides against *Pseudomonas aeruginosa*. Journal Antimicrobial Chemotherapy 36: 631-639.

C. Beaulac, S. Clement-Major, J. Hawari, J. Lagace (1997) In vitro kinetics of drug release and pulmonary retention of microencapsulated antibiotic in liposomal formulations in relation to the lipid composition. Journal Microencapsulation 14(3): 335-348.

P. Demaeyer, E.M. Akodad, E. Gravet, P. Schietecat, J.P. van Vooren, A. Drowart, J.C. Yernault, F.J. Legros (1993) Disposition of liposomal gentamicin following intrabronchial administration in rabbits. Journal Microencapsulation 10(1): 77-88.

M. Antos, E.A. Trafny, J. Gryzbowski (1995) Antibacterial activity of liposomal amikacin against *Pseudomonas aeruginosa* in vitro. Pharmacological Research 32(½): 84-87.

R.M. Schiffelers, G. Storm, I.A.J.M. Bakker-Woudenberg (2001) Therapeutic efficacy of liposomal gentamicin in clinically relevant rat models. International Journal Pharmaceutics 214: 103-105.

L.E. Bermudez, A.O. Yau-Young, J.-P. Lin, J. Cogger, L.S. Young (1999) Treatment of Disseminated Mycobacterium avium Complex Infection of Beige Mice with Liposome-Encapsulated Aminoglycosides. Journal Infect. Dis. 161: 1262-1268.

J.H. Zhang and J.B. Zhu (1999) A Novel Method to Prepare Liposomes Containing Amikacin. Journal Microencapsulation 16(4): 511-516.

S. Zeng, C. Hu, H. Wei, Y. Lu, Y. Zhang, J. Yang, G. Yun, W. Zou, B. Song (1993) Intravitreal Pharmacokinetics of Liposome-encapsulated Amikacin in a Rabbit Model. Opthamology 100: 1640-1644.

M.H. Cynamon, C.E. Swenson, G.S. Palmer, & R.S. Ginsberg (1989) Liposome-Encapsulated-Amikacin Therapy of Mycobacterium avium Complex Infection in Geige Mice. Antimicrobial Agents and Chemotherapy 33(8): 1179-1183.

R.M. Fielding, L. Moon-McDermott, R.O. Lewis, M.J. Horner (1999) Pharmacokinetics and Urinary Excretion of Amikacin in Low-Clearance Unilamellar Liposomes after a Single or Repeated Intravenous Administration in the Rhesus Monkey. Antimicrobial Agents and Chemotherapy 43(3): 503-509.

K. Yanagihara (2002) Design of anti-bacterial drug and anti-Mycobacterial drug for drug delivery system. Current Pharmaceutical Design 8: 475-482.

T.C. Whitehead, A.M. Lovering, L.M. Cropley, P. Wade, R.N. Davidson (1998) Kinetics and Toxicity of Liposomal and Conventional Amikacin in a Patient with Multidrug-Resistant Tuberculosis. Eur J Clin Microbiol Infect Dis 17: 794-797.

E. A. Petersen, J.B. Grayson, E.M. Hersh, R.T. Dorr, S.-M. Chiang, M. Oka, R.T. Proffitt (1996) Liposomal amikacin: improved treatment of Mycibacterium avium complex infection in the beige mouse model. Journal Antimicrobial Chemotherapy 38: 819-828.

A.A. Roehrborn, J.F. Hansbrough, B. Gauldoni, S. Kim. (1995) Lipid-based slow-release formulation of amikacin sulfate reduces foreign body associated infections in mice. Antimicrobial Agents Chemotherapy 39: 1752-1755.

S.B. Howell (2001) Clinical applications of a novel sustained-release injectable drug delivery system: Depofoam Technology. Cancer Journal 7: 219-227.

A. Omri & M. Ravaoarinoro (1996) Comparison of the Bactericidal Action of Amikacin, Netilmicin and Tobramtcin in Free and Liposomal Formulation against *Pseudomonas aeruginosa*. Chemotherapy 42: 170-176.

L. Kesavalu, J.A. Goldstein, R.J. Debs, N. Duzgunes, P.R.J. Gangadharam (1990) Differential effects of free and liposome encapsulated amikacin on the survival of *Mycobacterium avium* complex in mouse peritoneal macrophages. Tubercle 71: 215-218.

W.E. Bucke, S. Leitzke, J.E. Diederichs, K. Borner, H. Hahn, S. Ehlers, and R.H. Muller (1997) Surface-Modified Amikacin-Liposomes: Organ Distribution and Interaction with Plasma Proteins. Journal Drug Targeting 5(2): 99-108.

S. Ehlers, W. Bucke, S. Leitzke, L. Fortmann, D. Smith, H. Hansch, H. Hahn, G. Bancroff, and R. Muller (1996) Liposomal amikacin for treatment of *M. avium* Infections in clinically relevant experimental settings. Zbl. Bakt. 284: 218-231.

E.K. Kim and H.B. Kim (1990) Pharmacokinetics of intravitreally injected liposomes encapsulated tobramycin in normal rabbits. Yonsei Medical Journal 31(4): 308-314.

A. Omri, C. Beaulac, M. Bouhajib, S. Montplaisir, M. Sharkawi, J. Lagace (1994) Pulmonary retention of free and liposome-encapsulated tobramycin after intratracheal administration in uninfected rats and rats infected with *Pseudomonas aeruginosa*. Antimicrobial Agents and Chemotherapy 38(5) 1090-1095.

J.R. Morgan and K.E. Williams (1980) Preparation and properties of liposome-associated gentamicin. Antimicrobial Agents and Chemotherapy 17(4) 544-548.

P. Lutwyche, C. Cordeiro, D.J. Wiseman, M. St-Louis, M. Uh, M.J. Hope, M.S. Webb, B.B. Finlay (1998) Intracellular delivery and antibacterial activity of gentamicin encapsulated in pH-sensitive liposomes. Antimicrobial Agents and Chemotherapy 42(10) 2511-2520.

R.M. Schiffelers, G. Storm, M.T.T. Kate, L.E.T. Stearne-Cullen, J.G. Den Hollander, H.A. Verbrugh, I.A.J.M. Bakker-Woudenberg (2001) In vivo synergistic interaction of liposome-coencapsulated gentamicin and ceftazidime. Journal Pharmacology Experimental Therapeutics 298(1): 369-375.

A.I. Vitas, R. Diaz, and C. Gamazo (1996)Effect of composition and method of preparation of liposomes on their stability and interaction with murine monocytes infected with *Brucella abortus*. Antimicrobial Agents and Chemotherapy 40(1) 146-151.

E.A. Trafny, M. Stepinska, M. Antos, J. Grzybowski (1995) Effects of free and liposomes-encapsulated antibiotics on adherence of *Pseudomonas aeruginosa* to collagen type I. Antimicrobial Agents and Chemotherapy 39(12) 2645-2649.

S.P. Klemens, M.H. Cynamon, C.E. Swenson, R.S. Ginsberg (1990) Liposome-encapsulated-gentamicin therapy of *Mycobacterium avium* complex infection in beige mice. Antimicrobial Agents and Chemotherapy 34(6) 967-970.

S. D. Nightingale, S.L. Saletan, C.E. Swenson, A.J. Lawrence, D.A. Watson, F.G. Pilkiewicz, E.G. Silverman, S.X. Cal (1993) Liposome-encapsulated gentamicin treatment of *Mycobacterium avium-Mycobacterium intracellulare* complex bacteremia in AIDS patients. Antimicrobial Agents and Chemotherapy 37(9) 1869-1872.

C.E. Swenson, K.A. Stewart, J.L. Hammett, W.E. Fitzsimmons, R.S. Ginsberg (1990) Pharmacokinetics and in vivo activity of liposome-encapsulated gentamicin. Antimicrobial Agents and Chemotherapy 34(2) 235-240.

I.A.J.M. Bakker-Woudenberg, M.T. ten Kate, L.E.T. Stearne-Cullen, M.C. Woodle (1995) Efficacy of gentamicin or ceftazidine entrapped in liposomes with prolonged blood circulation and enhanced localization in *Klebsiella pneumoniae*-infected lung tissue. Journal Infectious Diseases 171:938-947.

M.W. Fountain, S.J. Weiss, A.G. Fountain, A. Shen, R.P. Lenk (1985) Treatment of *Brucella canis* and *Brucella abortus* in vitro and in vivo by stable plurilamellar vesicle-encapsulated aminoglycosides. Journal Infectious Diseases 152(3): 529-535.

C.I. Price, J.W. Horton, C.R. Baxter (1992) Liposome delivery of aminoglycosides in burn wounds. Surgery, Gynecology &Obstetrics 174: 414-418.

C.I. Price, J.W. Horton, C.R. Baxter (1994) Liposome encapsulation: a method for enhancing the effectiveness of local antibiotics. Surgery, 115(4) 480-4487.

C.I. Price, J.W. Horton, C.R. Baxter (1989) Enhanced effectiveness of intraperitoneal antibiotics administered via liposomal carrier. Arch Surgery 124: 1411-1415.

Alton et al., "Cationic lipid-mediated CFTR gene transfer to the lungs and nose of patients with cystic fibrosis: a double-blind placebo-controlled trial," The Lancet, 353:947-954 (1999).

Poyner et al., "A comparative study on the pulmonary delivery of tobramycin encapsulated into liposomes of PLA microspheres following intravenous and endotracheal delivery," Journal of Controlled Release, 35:41-48 (1995).

Schreier et al., "Pulmonary delivery of liposomes," Journal of Controlled Release, 24:209-233 (1993).

Sermet-Gaudelus et al., "Nebulized Antibiotics in Cystic Fibrosis," Paediatric Drugs, 4(7):455-467 (2002).

Supplementary European Search Report dated Jan. 12, 2009 for 03816990.0.

Beaulac et al., "Eradication of Mucoid *Pseudomonas aeruginosa* with Fluid Liposome-Encapsulated Tobramycin in an Animal Model of Chronic Pulmonary Infection," Antimicrobial Agents and Chemotherapy, 40(3):665-669 (1996).

Beaulac et al., "In-vitro bactericidal efficacy of sub-MIC concentrations of liposome-encapsulated antibiotic against Gram-negatie and Gram-positive bacteria," Journal of Antimicrobial Chemotherapy, 41:35-41 (1998).

* cited by examiner

SUSTAINED RELEASE OF ANTIINFECTIVES

This application claims the priority of U.S. Provisional Application 60/421,923, filed Oct. 29, 2002.

Certain sustained release technology suitable, for example, for administration by inhalation employs liposomes and lipid complexes to provide prolonged therapeutic effect of drug in the lung and systemically by sustained release and the ability to target and enhance the uptake of drug into sites of disease. The present invention comprises a liposomal antiinfective, and methods for treatment of pulmonary infections in cystic fibrosis (CF) patients using liposomal or lipid-complexed antiinfective. Unexpectedly, treatments with the new formulation require a significantly lower dosage than that known to have efficacy in the art.

As reported in Goodman and Gilman's The Pharmaceutical Basis of Therapeutics, Eighth Edition, "Since the incidence of nephrotoxicity and ototoxicity is related to the concentration to which an aminoglycoside accumulates, it is critical to reduce the maintenance dosage of these drugs in patients with impaired renal function." Since aminoglycosides can produce vestibular or auditory dysfunction and nephrotoxicity regardless of a patient's impairments, it is important generally to reduce maintenance dosages. The present invention provides dramatic reductions in maintenance dosages.

CF patients have thick mucous and/or sputum secretions in the lungs, frequent consequential infections, and biofilms resulting from bacterial colonizations. All these fluids and materials create barriers to effectively targeting infections with antiinfectives. The present invention overcomes these barriers, and even allows reduced dosing (in amount or frequency), thereby reducing the drug load on patients.

For lung infections generally, the dosing schedule provided by the invention provides a means of reducing drug load.

SUMMARY OF THE INVENTION

Provided, among other things, is a method of treating or ameliorating pulmonary infection in a cystic fibrosis patient comprising pulmonary administration of an effective amount of a liposomal/complexed antiinfective to the patient, wherein the (i) administrated amount is 50% or less of the comparative free drug amount, or (ii) the dosing is once a day or less, or (iii) both.

Also provided is a method of treating or ameliorating pulmonary infection in an animal comprising pulmonary administration of an effective amount of a liposomal/complexed antiinfective to the patient, wherein the (i) administrated amount is 50% or less of the comparative free drug amount, and (ii) the dosing is once every two days or less.

DETAILED DESCRIPTION OF THE INVENTION

Figure 1:
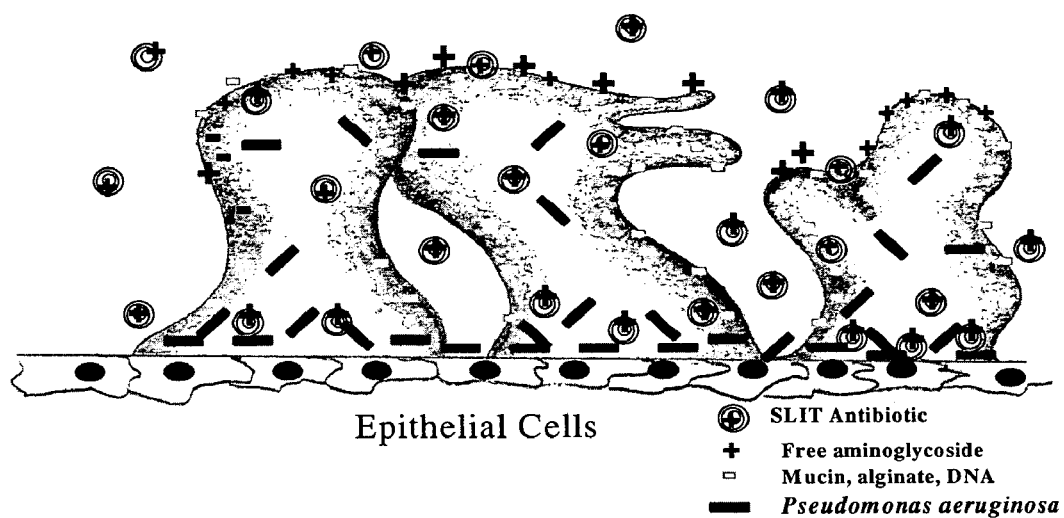
FIG. 1: Cross sectional diagram of the sputum/biofilm seen in patients with cystic fibrosis.

The present application discloses a method of treating or ameliorating pulmonary infections, such as in cystic fibrosis patients, comprising administration of antiinfective (such as antibiotic) encapsulated in lipid-based particles.

Antiinfectives are agents that act against infections, such as bacterial, mycobacterial, fungal, viral or protozoal infections.

Antiinfectives covered by the invention include but are not limited to aminoglycosides (e.g., streptomycin, gentamicin, tobramycin, amikacin, netilmicin, kanamycin, and the like), tetracyclines (such as chlortetracycline, oxytetracycline, methacycline, doxycycline, minocycline and the like), sulfonamides (e.g., sulfanilamide, sulfadiazine, sulfamethaoxazole, sulfisoxazole, sulfacetamide, and the like), para-aminobenzoic acid, diaminopyrimidines (such as trimethoprim, often used in conjunction with sulfamethoxazole, pyrazinamide, and the like), quinolones (such as nalidixic acid, cinoxacin, ciprofloxacin and norfloxacin and the like), penicillins (such as penicillin G, penicillin V, ampicillin, amoxicillin, bacampicillin, carbenicillin, carbenicillin indanyl, ticarcillin, azlocillin, mezlocillin, piperacillin, and the like), penicillinase resistant penicillin (such as methicillin, oxacillin, cloxacillin, dicloxacillin, nafcillin and the like), first generation cephalosporins (such as cefadroxil, cephalexin, cephradine, cephalothin, cephapirin, cefazolin, and the like), second generation cephalosporins (such as cefaclor, cefamandole, cefonicid, cefoxitin, cefotetan, cefuroxime, cefuroxime axetil, cefinetazole, cefprozil, loracarbef, ceforanide, and the like), third generation cephalosporins (such as cefepime, cefoperazone, cefotaxime, ceftizoxime, ceftriaxone, ceftazidime, cefixime, cefpodoxime, ceftibuten, and the like), other beta-lactams (such as imipenem, meropenem, aztreonam, clavulanic acid, sulbactam, tazobactam, and the like), beta-lactamase inhibitors (such as clavulanic acid), chloramphenicol, macrolides (such as erythromycin, azithromycin, clarithromycin, and the like), lincomycin, clindamycin, spectinomycin, polymyxin B, polymixins (such as polymyxin A, B, C, D, $E_1$(colistin A), or $E_2$, colistin B or C, and the like) colistin, vancomycin, bacitracin, isoniazid, rifampin, ethambutol, ethionamide, aminosalicylic acid, cycloserine, capreomycin, sulfones (such as dapsone, sulfoxone sodium, and the like), clofazimine, thalidomide, or any other antibacterial agent that can be lipid encapsulated. Antiinfectives can include antifungal agents, including polyene antifungals (such as amphotericin B, nystatin, natamycin, and the like), flucytosine, imidazoles (such as miconazole, clotrimazole, econazole, ketoconazole, and the like), triazoles (such as itraconazole, fluconazole, and the like), griseofulvin, terconazole, butoconazole ciclopirax, ciclopirox olamine, haloprogin, tolnaftate, naftifine, terbinafine, or any other antifungal that can be lipid encapsulated or complexed. Discussion and the examples are directed primarily toward amikacin but the scope of the application is not intended to be limited to this antiinfective. Combinations of drugs can be used.

Particularly preferred antiinfectives include the aminoglycosides, the quinolones, the polyene antifungals and the polymyxins.

Among the pulmonary infections (such as in cystic fibrosis patients) that can be treated with the methods of the invention are pseudomonas (e.g., *P. aeruginosa, P. paucimobilis, P. putida, P. fluorescens*, and *P. acidovorans*), staphylococcal, Methicillin-resistant *Staphylococcus aureus* (MRSA), streptococcal (including by *Streptococcus pneumoniae*), *Escherichia coli, Klebsiella, Enterobacter, Serratia, Haemophilus, Yersinia pestis, Burkholderia pseudomallei, B. cepacia, B. gladioli, B. multivorans, B. vietnamiensis, Mycobacterium*

*tuberculosis, M. avium* complex (MAC)(*M. avium* and *M. intracellulare*), *M. kansasii, M. xenopi, M. marinum, M. ulcerans*, or *M. fortuitum* complex (*M. fortuitum* and *M. chelonei*) infections.

In one preferred embodiment the present invention comprises a method of treatment comprising administration of liposomal/complexed amikacin.

The "liposomal or lipid-complexed" antiinfective, or "liposomal/complexed" antiinfective, or "Lip-antiinfective," or "Lip-An" discussed herein is any form of antiinfective composition where at least about 1% by weight of the antiinfective is associated with the lipid either as part of a complex with the lipid, or as a liposome where the antibiotic may be in the aqueous phase or the hydrophobic bilayer phase or at the interfacial headgroup region of the liposomal bilayer. Preferably, at least about 5%, or at least about 10%, or at least about 20%, or at least about 25%, is so associated. Association is measured by separation through a filter where lipid and lipid-associated drug is retained and free drug is in the filtrate.

Treatment with liposomal/complexed antiinfective requires a notably lower dosage than prior known treatments. In one preferred embodiment less than 100 mg per day of an aminoglycoside is administered to humans. In another preferred embodiment approximately 30 to 50 mg is administered every other day or every third day. It is expected that dosages can be correspondingly lowered for other species as compared to the dosage recommended for antiinfective that is not liposomal or lipid-complexed. This is an unexpectedly low dosage.

Where no specific dosage is provided below, the preferred dosage of the invention is 50% or less, 35% or less, 20% or less, or 10% or less, of the minimum free drug (which of course can be a salt) amount that is effective, if delivered to the lungs via a nebulizer, to reduce the CFU count in the lungs by one order of magnitude over the course of a 14-day treatment. The comparative free drug amount is the cumulative amount that would be used in the dosing period applied with the drug administration of the invention. The comparative minimum free drug defined in this paragraph is a "comparative free drug amount."

The non-CF treating embodiments of the invention can be used with any animal, though preferably with humans. Relative amounts in a given animal are measured with respect to such animal.

The dosing schedule is preferably once a day or less. In preferred embodiments, the dosing schedule is once every other day, every third day, every week, or less. For example, the dosing schedule can be every other day or less, using 50% or less of the comparative free drug amount. Or, for example, the dosing can be daily using 35% or less of the comparative free drug amount.

To treat the infections of the invention, an effective amount of a pharmaceutical compound will be recognized by clinicians but includes an amount effective to treat, reduce, ameliorate, eliminate or prevent one or more symptoms of the disease sought to be treated or the condition sought to be avoided or treated, or to otherwise produce a clinically recognizable change in the pathology of the disease or condition. Amelioration includes reducing the incidence or severity of infections in animals treated prophylactically. In certain embodiments, the effective amount is one effective to treat or ameliorate after symptoms of lung infection have arisen. In certain other embodiments, the effective amount is one effective to treat or ameliorate the average incidence or severity of infections in animals treated prophylactically (as measured by statistical studies).

Liposome or other lipid based delivery systems can be administered for inhalation either as a nebulized spray, powder, or aerosol, or by intrathecal administration. Inhalation administrations are preferred. The overall result is a less frequent administration and an enhanced therapeutic index compared to free drug or parenteral form of the drug. Liposomes or lipid complexes are particularly advantageous due to their ability to protect the drug while being compatible with the lung lining or lung surfactant.

The present invention includes methods for treatment of pulmonary gram-negative infections. One usefully treated infection is chronic pseudomonal infection in CF patients. Known treatments of lung infections (such as in CF patients) with amikacin generally comprise administering approximately 200-600 mg of amikacin or tobramycin per day via inhalation. The present invention allows for treatment by administering, in one preferred embodiment, 100 mg or less of amikacin per day (or normalized to 100 mg per day or less if dosing less frequent). In yet another embodiment administration of 60 mg or less of amikacin every day is performed. And in still another embodiment administration of approximately 30 to 50 mg not more than once every 2 days is performed. The most preferred embodiment comprises administration of approximately 30 to 50 mg every other day or every third day.

Known treatments of lung infections with tobramycin generally comprise administering 300 mg, twice a day, in adults and children 6 years of age or older. The present invention allows for treatment by administering, in one preferred embodiment, 100 mg or less of tobramycin per day. In yet another embodiment administration of 60 mg or less of tobramycin every day is performed. And in still another embodiment administration of approximately 30 to 50 mg not more than once every 2 days is performed. The most preferred embodiment comprises administration of approximately 30 to 50 mg every other day or every third day.

The lipids used in the compositions of the present invention can be synthetic, semi-synthetic or naturally-occurring lipids, including phospholipids, tocopherols, steroids, fatty acids, glycoproteins such as albumin, negatively-charged lipids and cationic lipids. Phosholipids include egg phosphatidylcholine (EPC), egg phosphatidylglycerol (EPG), egg phosphatidylinositol (EPI), egg phosphatidylserine (EPS), phosphatidylethanolamine (EPE), and egg phosphatidic acid (EPA); the soya counterparts, soy phosphatidylcholine (SPC); SPG, SPS, SPI, SPE, and SPA; the hydrogenated egg and soya counterparts (e.g., HEPC, HSPC), other phospholipids made up of ester linkages of fatty acids in the 2 and 3 of glycerol positions containing chains of 12 to 26 carbon atoms and different head groups in the 1 position of glycerol that include choline, glycerol, inositol, serine, ethanolamine, as well as the corresponding phosphatidic acids. The chains on these fatty acids can be saturated or unsaturated, and the phospholipid can be made up of fatty acids of different chain lengths and different degrees of unsaturation. In particular, the compositions of the formulations can include dipalmitoylphosphatidylcholine (DPPC), a major constituent of naturally-occurring lung surfactant as well as dioleoylphosphatidylcholine (DOPC). Other examples include dimyristoylphosphatidylcholine (DMPC) and dimyristoylphosphatidylglycerol (DMPG) dipalmitoylphosphatidcholine (DPPC) and dipalmitoylphosphatidylglycerol (DPPG) distearoylphosphatidylcholine (DSPC) and distearoylphosphatidylglycerol (DSPG), dioleylphosphatidylethanolamine (DOPE) and mixed phospholipids like palmitoylstearoylphosphatidylcholine (PSPC) and palmitoylstearoylphosphatidylglycerol (PSPG), triacylglycerol, diacylglycerol, seranide, sphingosine, sphingomyelin and single acylated phospholipids like mono-oleoyl-phosphatidylethanolamine (MOPE).

The lipids used can include ammonium salts of fatty acids, phospholipids and glycerides, steroids, phosphatidylglycerols (PGs), phosphatidic acids (PAs), phosphotidylcholines (PCs), phosphatidylinositols (Pls) and the phosphatidylserines (PSs). The fatty acids include fatty acids of carbon chain lengths of 12 to 26 carbon atoms that are either saturated or unsaturated. Some specific examples include: myristylamine, palmitylamine, laurylamine and stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9 (Z)-octadecenyloxy)-prop-1-yl-N,N,N-trimethylammonium chloride (DOTMA) and 1, 2-bis(oleoyloxy)-3-(trimethylammonio)propane (DOTAP). Examples of steroids include cholesterol and ergosterol. Examples of PGs, PAs, PIs, PCs and PSs include DMPG, DPPG, DSPG, DMPA, DPPA, DSPA, DMPI, DPPI, DSPI, DMPS, DPPS and DSPS, DSPC, DPPC, DMPC, DOPC, egg PC.

Liposomes or lipid complexes composed of phosphatidylcholines, such as DPPC, aid in the uptake by the cells in the lung such as the alveolar macrophages and helps to sustain release of the antiinfective agent in the lung (Gonzales-Rothi et al. (1991)). The negatively charged lipids such as the PGs, PAs, PSs and PIs, in addition to reducing particle aggregation, can play a role in the sustained release characteristics of the inhalation formulation as well as in the transport of the formulation across the lung (transcytosis) for systemic uptake. The sterol compounds are believed to affect the release and leakage characteristics of the formulation.

Liposomes are completely closed lipid bilayer membranes containing an entrapped aqueous volume. Liposomes can be unilamellar vesicles (possessing a single membrane bilayer) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "heads" orient towards the aqueous phase. Lipid complexes are associations between lipid and the antiinfective agent that is being incorporated. This association can be covalent, ionic, electrostatic, noncovalent, or steric. These complexes are non-liposomal and are incapable of entrapping additional water soluble solutes. Examples of such complexes include lipid complexes of amphotericin B (Janoff et al., Proc. Nat Acad. Sci., 85:6122 6126, 1988) and cardiolipin complexed with doxorubicin.

A lipid clathrate is a three-dimensional, cage-like structure employing one or more lipids wherein the structure entraps a bioactive agent. Such clathrates are included in the scope of the present invention.

Proliposomes are formulations that can become liposomes or lipid complexes upon coming in contact with an aqueous liquid. Agitation or other mixing can be necessary. Such proliposomes are included in the scope of the present invention.

Liposomes can be produced by a variety of methods (for example, see, Bally, Cullis et al., Biotechnol Adv. 5(1):194, 1987). Bangham's procedure (J. Mol. Biol., J Mol Biol. 13(1):238-52, 1965) produces ordinary multilamellar vesicles (MLVs). Lenk et al. (U.S. Pat. Nos. 4,522,803, 5,030, 453 and 5,169,637), Fountain et al. (U.S. Pat. No. 4,588,578) and Cullis et al. (U.S. Pat. No. 4,975,282) disclose methods for producing multilamellar liposomes having substantially equal interlamellar solute distribution in each of their aqueous compartments. Paphadjopoulos et al., U.S. Pat. No. 4,235,871, discloses preparation of oligolamellar liposomes by reverse phase evaporation.

Unilamellar vesicles can be produced from MLVs by a number of techniques, for example, the extrusion of Cullis et al. (U.S. Pat. No. 5,008,050) and Loughrey et al. (U.S. Pat. No. 5,059,421). Sonication and homogenization can be used to produce smaller unilamellar liposomes from larger liposomes (see, for example, Paphadjopoulos et al., Biochim. Biophys. Acta., 135:624-638, 1967; Deamer, U.S. Pat. No. 4,515,736; and Chapman et al., Liposome Technol., 1984, pp. 1-18).

The original liposome preparation of Bangham et al. (J. Mol. Biol., 1965, 13:238-252) involves suspending phospholipids in an organic solvent which is then evaporated to dryness leaving a phospholipid film on the reaction vessel. Next, an appropriate amount of aqueous phase is added, the mixture is allowed to "swell", and the resulting liposomes which consist of multilamellar vesicles (MLVs) are dispersed by mechanical means. This preparation provides the basis for the development of the small sonicated unilamellar vesicles described by Papahadjopoulos et al. (Biochim. Biophys, Acta., 1967, 135:624-638), and large unilamellar vesicles.

Techniques for producing large unilamellar vesicles (LUVs), such as, reverse phase evaporation, infusion procedures, and detergent dilution, can be used to produce liposomes. A review of these and other methods for producing liposomes can be found in the text Liposomes, Marc Ostro, ed., Marcel Dekker, Inc., New York, 1983, Chapter 1, the pertinent portions of which are incorporated herein by reference. See also Szoka, Jr. et al., (1980, Ann. Rev. Biophys. Bioeng., 9:467), the pertinent portions of which are also incorporated herein by reference.

Other techniques that are used to prepare vesicles include those that form reverse-phase evaporation vesicles (REV), Papahadjopoulos et al., U.S. Pat. No. 4,235,871. Another class of liposomes that can be used are those characterized as having substantially equal lamellar solute distribution. This class of liposomes is denominated as stable plurilamellar vesicles (SPLV) as defined in U.S. Pat. No. 4,522,803 to Lenk, et al. and includes monophasic vesicles as described in U.S. Pat. No. 4,588,578 to Fountain, et al. and frozen and thawed multilamellar vesicles (FATMLV) as described above.

A variety of sterols and their water soluble derivatives such as cholesterol hemisuccinate have been used to form liposomes; see specifically Janoff et al., U.S. Pat. No. 4,721,612, issued Jan. 26, 1988, entitled "Steroidal Liposomes." Mayhew et al, described a method for reducing the toxicity of antibacterial agents and antiviral agents by encapsulating them in liposomes comprising alpha-tocopherol and certain derivatives thereof. Also, a variety of tocopherols and their water soluble derivatives have been used to form liposomes, see Janoff et al., U.S. Pat. No. 5,041,278.

A process for forming liposomes or lipid complexes involves a "solvent infusion" process. This is a process that includes dissolving one or more lipids in a small, preferably minimal, amount of a process compatible solvent to form a lipid suspension or solution (preferably a solution) and then injecting the solution into an aqueous medium containing bioactive agents. Typically a process compatible solvent is one that can be washed away in a aqueous process such as dialysis. The composition that is cool/warm cycled is preferably formed by solvent infusion, with ethanol infusion being preferred. Alcohols are preferred as solvents. "Ethanol infusion," a type of solvent infusion, is a process that includes dissolving one or more lipids in a small, preferably minimal, amount of ethanol to form a lipid solution and then injecting the solution into an aqueous medium containing bioactive agents. A "small" amount of solvent is an amount compatible with forming liposomes or lipid complexes in the infusion process. Such processes are described in Lee et al., U.S. patent application Ser. No. 10/634,144, filed Aug. 4, 2003, Pilkiewicz et al, U.S. patent application Ser. No. 10/383,173, filed Mar. 5, 2003, and Boni et al., U.S. patent application Ser. No. 10/383,004, filed Mar. 5, 2003, which applications are hereby incorporated by reference in their entirety.

Liposome or lipid complex sizing can be accomplished by a number of methods, such as extrusion, sonication and homogenization techniques which are well known, and readily practiced, by ordinarily skilled artisans. Extrusion involves passing liposomes, under pressure, one or more times through filters having defined pore sizes. The filters are generally made of polycarbonate, but the filters may be made of any durable material which does not interact with the liposomes and which is sufficiently strong to allow extrusion under sufficient pressure. Preferred filters include "straight through" filters because they generally can withstand the higher pressure of the preferred extrusion processes of the present invention. "Tortuous path" filters may also be used. Extrusion can also use asymmetric filters, such as AnotecO™ filters, which involves extruding liposomes through a branched-pore type aluminum oxide porous filter.

Liposomes or lipid complexes can also be size reduced by sonication, which employs sonic energy to disrupt or shear liposomes, which will spontaneously reform into smaller liposomes. Sonication is conducted by immersing a glass tube containing the liposome suspension into the sonic epicenter produced in a bath-type sonicator. Alternatively, a probe type sonicator may be used in which the sonic energy is generated by vibration of a titanium probe in direct contact with the liposome suspension. Homogenization and milling apparatii, such as the Gifford Wood homogenizer, Polytron™ or Microfluidizer™, can also be used to break down larger liposomes or lipid complexes into smaller liposomes or lipid complexes.

The resulting liposomes/complexes can be separated into homogeneous populations using methods well known in the art; such as tangential flow filtration. In this procedure, a heterogeneously sized population of liposomes or lipid complexes is passed through tangential flow filters, thereby resulting in a liposome population with an upper and/or lower size limit. When two filters of differing sizes, that is, having different pore diameters, are employed, liposomes smaller than the first pore diameter pass through the filter. This filtrate can the be subject to tangential flow filtration through a second filter, having a smaller pore size than the first filter. The retentate of this filter is a liposomal/complexe population having upper and lower size limits defined by the pore sizes of the first and second filters, respectively.

Mayer et al. found that the problems associated with efficient entrapment of lipophilic ionizable bioactive agents such as antineoplastic agents, for example, anthracyclines or vinca alkaloids, can be alleviated by employing transmembrane ion gradients. Aside from inducing greater uptake, such transmembrane gradients can also act to increase antiinfective retention in the liposomes/complexes.

Liposomal/complexed antiinfective has a sustained antiinfective effect and lower toxicity allowing less frequent administration and an enhanced therapeutic index. In preclinical animal studies and in comparison to inhaled Tobramycin (not liposomal or lipid-complexed) at the equivalent dose level, liposomal/complexed amikacin was shown to have, during the time period shortly after administration to over 24 hours later, drug levels in the lung that ranged from two to several hundred times that of Tobramycin. Additionally, liposomal/complexed amikacin maintained these levels for well over 24 hours. In an animal model designed to mimic the pseudomonas infection seen in CF patients, liposomal/complexed amikacin was shown to significantly eliminate the infection in the animals' lungs when compared to free aminoglycosides.

Lung surfactant allows for the expansion and compression of the lungs during breathing. This is accomplished by coating the lung with a combination of lipid and protein. The lipid is presented as a monolayer with the hydrophobic chains directed outward. The lipid represents 80% of the lung surfactant, the majority of the lipid being phosphatidylcholine, 50% of which is dipalmitoyl phosphatidylcholine (DPPC) (Veldhuizen et al, 1998). The surfactant proteins (SP) that are present function to maintain structure and facilitate both expansion and compression of the lung surfactant as occurs during breathing. Of these, SP-B and SP-C specifically have lytic behavior and can lyse liposomes (Hagwood et al., 1998; Johansson, 1998). This lytic behavior is believed to facilitate the gradual break-up of liposomes followed, by their release of internal contents allowing for a depot effect. This break-up of liposomes occurs naturally as evidenced by the spontaneous unraveling of lamellar bodies ejected by exocytosis (Ikegami & Jobe, 1998) In addition to becoming assimilated within the lung surfactant, liposomes can be directly ingested by macrophages through phagocytosis (Couveur et al., 1991; Gonzales-Roth et al., 1991; Swenson et al, 1991). Uptake of liposomes by alveolar macrophages is another means by which drugs can be delivered to the diseased site.

The lipids preferably used to form either liposomes or lipid complexes for inhalation use are common to the endogenous lipids found in the lung surfactant. Liposomes are composed of bilayers that entrap the desired pharmaceutical. These can be configured as multilamellar vesicles of concentric bilayers with the pharmaceutical trapped within either the lipid of the different layers or the aqueous space between the layers. The present invention unique processes to create unique liposomes and lipid/drug complexes. Both the processes and the product of these processes are part of the present invention.

The lipid to drug ratio using the process of the present invention is preferably less than 3 to 1. And more preferably the lipid to drug ratio is less than 2.5 to 1. Further the percentage of free antiinfective, present after the product is dialyzed for a particular duration, is decreased.

All processes described herein can be easily adapted for large scale, aseptic manufacture. The final liposome size can be adjusted by modifying the lipid composition, concentration, excipients, and processing parameters.

An obstacle to treating infectious diseases such as *Pseudomonas aeruginosa*, the leading cause of chronic illness in cystic fibrosis patients is drug penetration within the sputum/biofilm barrier on epithelial cells (FIG. 1). In FIG. 1, the donut shapes represent liposomal/complexed antiinfective, the "+" symbol represents free antiinfective, the "−" symbol mucin, alginate and DNA, and the solid bar symbol represents *Pseudomonas aeruginosa*. This barrier is composed of both colonized and planktonic *P. aeruginosa* embedded in alginate or exopolysaccharides from bacteria, as well as DNA from damaged leukocytes, and mucin from lung epithelial cells, all possessing a net negative charge (Costerton, et al., 1999). This negative charge binds up and prevent penetration of positively charged drugs such as aminoglycosides, rendering them biologically ineffective (Mendelman et al., 1985). Entrapment of antiinfectives within liposomes or lipid complexes could shield or partially shield the antiinfectives from non-specific binding to the sputum/biofilm, allowing for liposomes or lipid complexes (with entrapped aminoglycoside) to penetrate (FIG. 1).

Amikacin has been shown to have a high degree of resistance to bacterial enzymes, thus providing a greater percent of susceptible clinical isolates than found for other aminoglycosides including tobramycin and gentamicin (Price et al., 1976). In particular, P. aeruginosa isolates are far more sensitive to amikacin than other aminoglycosides while exhibiting no cross-resistance (Damaso et al., 1976).

Figure 2:
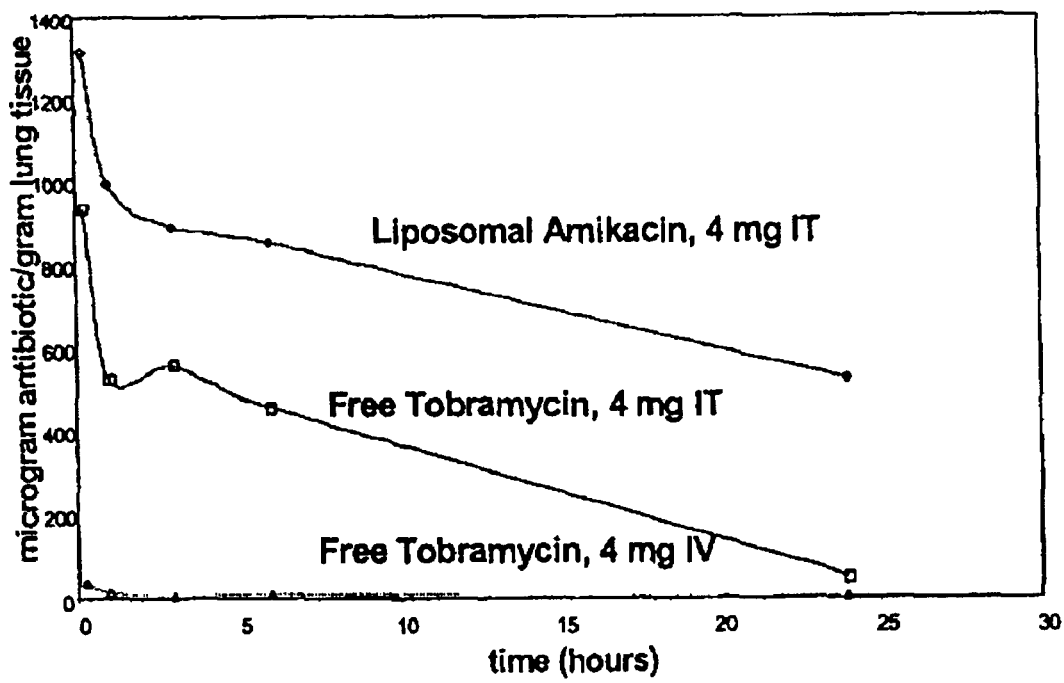
FIG. 2: Graphical representation of the targeting and depot effect of the drug of the present invention.

The sustained release and depot effect of liposomal/complexed amikacin is clearly seen in FIG. 2. In this study rats were given tobramycin via intratracheal and intravenous administration. The rats were also given liposomal/complexed amikacin intratracheally at the same dose (4 mg/rat). The data show that it is only with the liposomal/complexed amikacin that a sustained release and depot effect is achieved. In fact, 24 hours after dosing, only liposomal/complexed amikacin shows significant levels of the drug in the animal's lungs, while both tobramycin formulations revealed negligible levels, primarily due, it is believed to rapid systemic absorption. This greater than a hundred-fold increase of aminoglycoside in the lung for liposomal/complexed antiinfective supports the idea of a sustained release liposomal/complexed antiinfective that can be taken significantly less often than the currently approved TOBI™ formulation (Chiron Corporation, Ameryville, Calif.).

Moreover, the presence of a sputum/biofilm prevents the penetration of the free aminoglycosides due to binding of the antiinfectives to its surface (FIG. 1). Therefore, doses in excess of 1000 μg of tobramycin/gram of lung tissue are needed to show a therapeutic effect in CF patients. This is overcome with liposomal/complexed amikacin. Thus, the therapeutic level of drug is maintained for a longer period of time in the liposomal/complexed formulations of amikacin compared to free tobramycin. This facilitation of binding and penetration could also be a means by which liposomal/complexed amikacin could significantly reduce bacterial resistance commonly seen to develop when antibacterials are present in vivo at levels below the minimum inhibitory concentration.

The pharmacokinetics of amikacin was determined in rats following intratracheal (IT) administration of either free tobramycin or liposomal/complexed amikacin. These data were compared to the distribution obtained in the lungs following a tail vein injection of free tobramycin. In all cases a dose of 4 mg/rat was administered. As can be seen in FIG. 2, a much larger deposition of aminoglycoside can be delivered by IT compared to injection. The depot effect of liposomal/complexed antiinfective technology is also demonstrated in that in comparison to tobramycin given either IT or IV, a greater than a hundred-fold increase in drug for liposomal/complexed amikacin still remains in the lungs twenty-four hours following administration. Thus, the therapeutic level of drug is maintained for a longer period of time in the liposomal formulations of amikacin compared to free tobramycin.

The binding of aminoglycosides to sputum of CF patients is a concern, particularly if this binding reduces the bioactivity of the antiinfective (Hunt et al., 1995). To determine whether liposomal/complexed amikacin can retain biological activity over a prolonged period of time, normal rats were administered liposomal/complexed amikacin by intratracheal instillation. This was followed by its removal at 2 or 24 hours via a bronchial alveolar lavage (BAL) to determine biological activity. Samples were concentrated by ultrafiltration followed by filtration (0.2 micron) to remove contaminating lung microbes. Amikacin concentration was determined employing a TDX instrument and biological activity determined using a Mueller Hinton broth dilution assay (Pseudomonas aeruginosa). The results are shown in the following Table I:

| time (hours) | amakacin in BAL (microgram/mL) | amakacin in filtrate (microgram/mL) | MIC (μg/mL) |
|---|---|---|---|
| 2 | 160 | 119 | 1.9 |
| 24 | 73 | 32 | 4.0 |

As shown by the above table, the recovered filtered liposomal/complexed amikacin was capable of killing P. aeruginosa in a Mueller Hinton broth assay even after 24 hours with an MIC of 4. At 2 hours an MIC of 2 was obtained, which is similar to that obtained for the filtered liposomal/complexed amikacin stock. Thus, the liposomal/complexed amikacin was still active following 24 hours in the lung. At 24 hours free tobramycin at the same dose was undetectable in a BAL. This indicates that not only is the liposomal/complexed antiinfective formulation retained in the lung, but it is also freely available to penetrate a sputum/biofilm over time. These data combined with the facts as evident in FIG. 2 and Table II (below), that liposomal/complexed amikacin releases the free antiinfective over time while maintaining high levels of the antiinfective in the lungs, supports the rationale that this system may yield a sustained antiinfective effect over time. This effect should prove significant in reducing both the bioburden of the Pseudomonas and the development of resistance due to trough levels of antiinfective.

As an in vitro demonstration of slow release of liposomal/complexed amikacin and its sustained antiinfective effect, the formulation was incubated in sputum from patients with Chronic Obstructive Pulmonary Disease (COPD) containing PAO1 mucoid Pseudomonas. The liposomal/complexed amikacin was also incubated in alginate containing PAO1 mucoid Pseudomonas. In both cases sustained and enhanced killing of the pseudomonas over time was observed, as shown in Table II:

| In Vitro Sputum/Alginate Assay (% survival of PA01 Mucoid Pseudomonas) | | | | | |
|---|---|---|---|---|---|
| | Incubation time at 37° C. | | | | Amikacin conc. |
| | 1 h | 3 h | 6 h | 24 h | (microgram/mL) |
| Lip-An-15 Sputum | 81 | 15 | 22 | <1 | 8 |
| Lip-An-15 Alginate | 100 | 59 | 1 | <1 | 10 |

Classical kill curves are not applicable for liposomal/complexed antiinfective technology because the liposomal formulations exhibit a slow release of antiinfective with an enhanced antiinfective effect. The liposome/complex protects the amikacin from the sputum and/or alginate until its release. In time, complete killing is observed, consistent with slow release sustained antiinfective effect model with no interference or inactivation of antiinfective.

The efficacy of liposomal/complexed amikacin formulations was studied using a model for chronic pulmonary infection (Cash et al., 1979) where P. aeruginosa, embedded in an agarose bead matrix, was instilled in the trachea of rats. This mucoid Pseudomonas animal model was developed to resemble the *Pseudomonas* infections seen in CF patients. Some of the clinical correlates to CF include: a similar lung pathology; the development of immune complex disorders; and a conversion to the mucoid phenotype by *P. aeruginosa* strains (Cantin and Woods, 1999). Rat lungs were infected with over $10^7$ CFUs of a mucoid *Pseudomonas* (strain PAO1) taken from a CF patient isolate, and subsequently treated with (a) free aminoglycoside, (b) the lipid vehicle alone as nondrug control, and (c) liposomal/complexed amikacin. In addition, formulations were first screened on the ability to kill in vitro *P. aeruginosa* on modified Kirby-Bauer plates.

Figure 3:
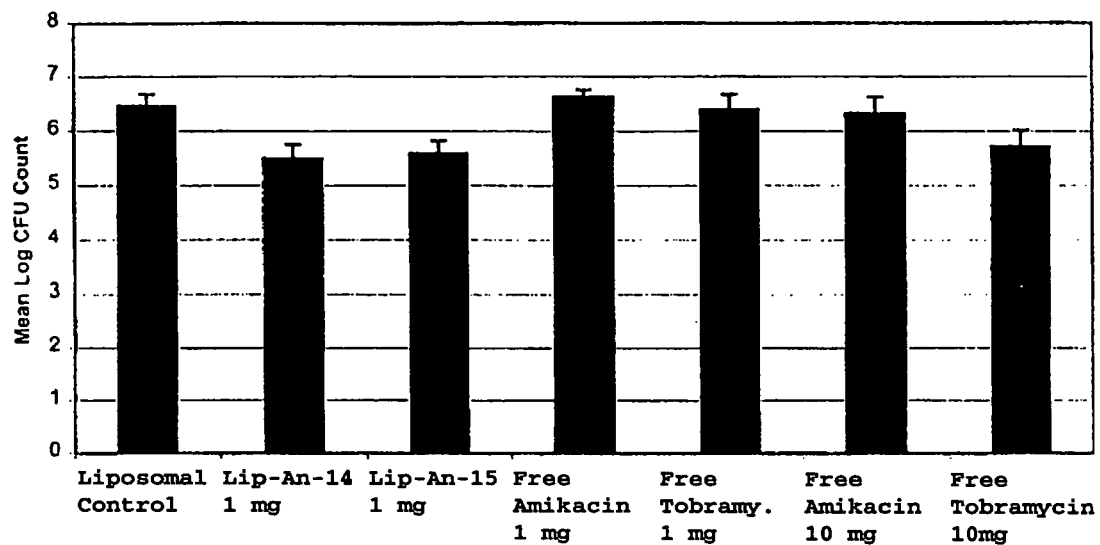
FIGS. 3 and 4: Graphical representations of bacteriology of amikacin in various forms.

Various liposomal/complexed amikacin formulations were tested based on either different lipid compositions or manufacturing parameters resulting in different killing zones in in vitro experiments. This experiment was designed to determine the increase in efficacy obtained with liposomal/complexed aminoglycoside over free aminoglycoside. Blank control lipid compositions, two different liposomal/complexed amikacin formulations and free amikacin and free Tobramycin at the same aminoglycoside concentrations as the liposomal/complexed antiinfective formulations were compared. In addition, a 10 fold higher dose of free amikacin and a 10 fold higher dose of free tobramycin were also given. Dosing was IT daily over seven days. Results (FIG. 3) indicate that liposomal/complexed amikacin in the two formulations (differing in lipid composition) revealed a significant reduction in CFU levels and were better at reducing CFUs than free amikacin or free tobramycin at 10-fold higher dosages. In the Figure, Lip-An-14 is DPPC/ChoVDOPC/DOPG (42:45:4:9) and 10 mg/ml amikacin, Lip-An-15 is DDPC/Chol (1:1) also at 10 mg/ml. All lipid-lipid and lipid-drug ratios herein are weight to weight.

Figure 4:
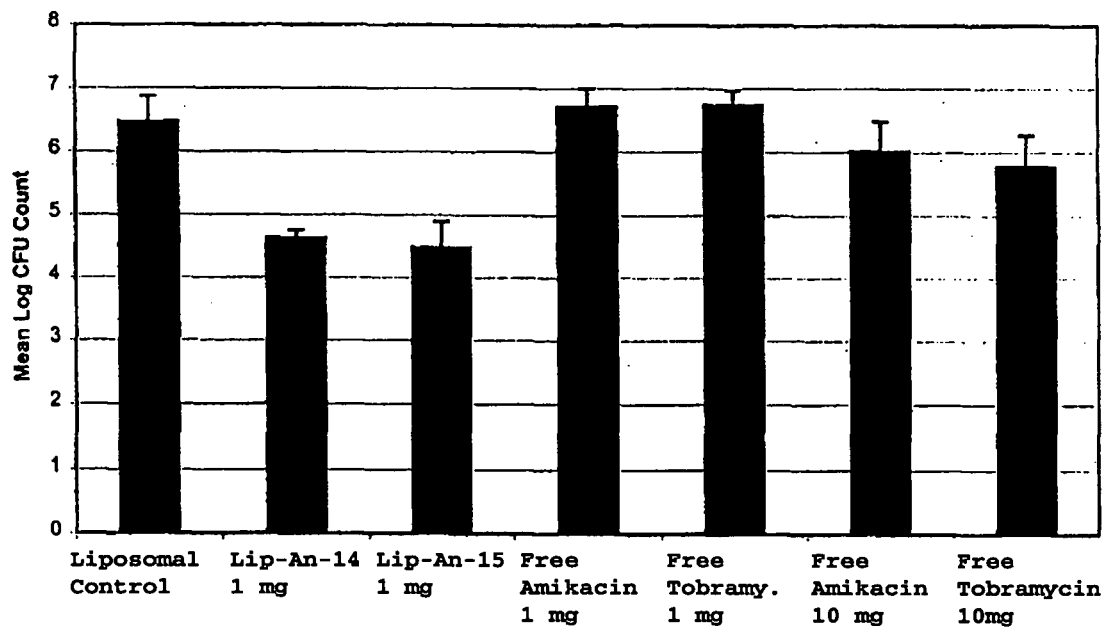
Figure 5:
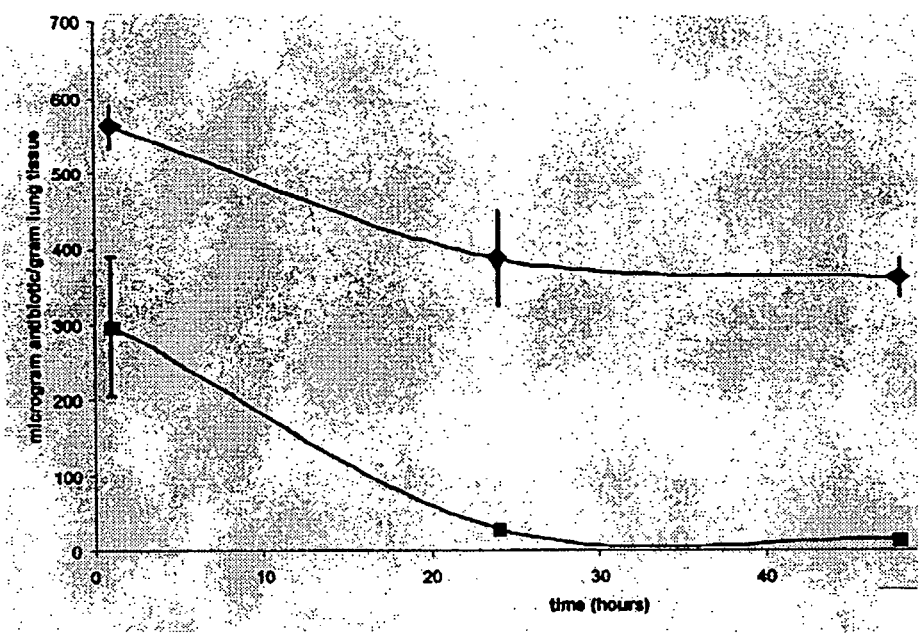
FIG. 5: Graphical representation of sustained release for liposomal/complexed amikacin and tobramycin.
Figure 6:
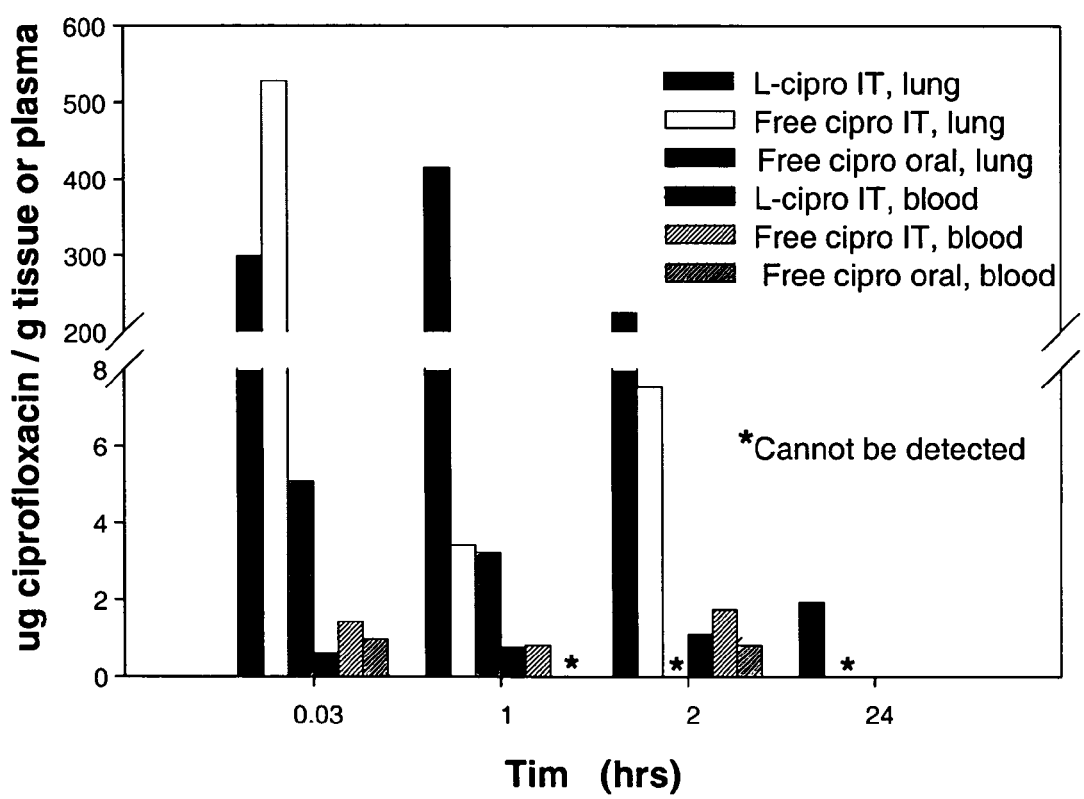
FIG. 6: Data on free or complexed ciprofloxacin.
Figure 7:
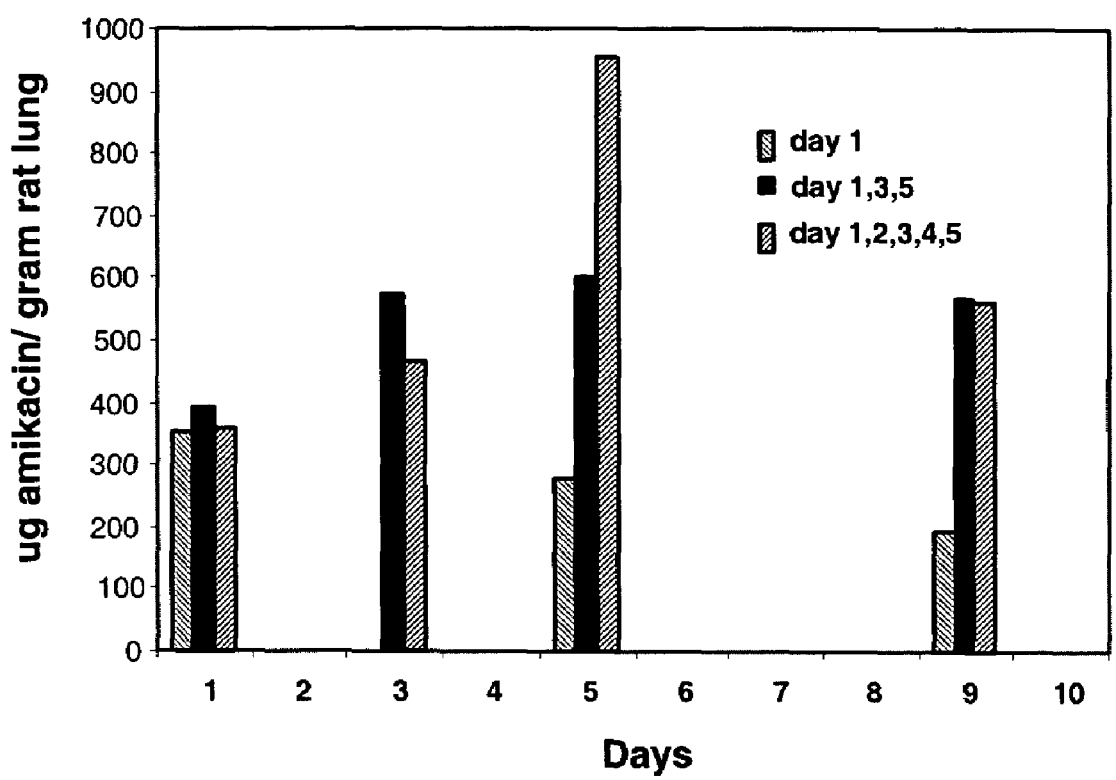
FIG. 7: Graphical representation of drug residence in the lung given various dosing schedules.

The next experiment (FIG. 4) was designed to demonstrate the slow release and sustained antiinfective capabilities of liposomal/complexed amikacin. The dosing was every other day for 14 days, as opposed to every day for seven days as in the previous experiments. Results indicate that liposomal/complexed amikacin in the two formulations (differing in lipid composition) had a 10 to 100 times more potent (greater ability to reduce CFU levels) than free amikacin or free tobramycin. A daily human dose of 600 mg TOBI® (or about 375 mg/m2) corresponds to a daily rat dose of 9.4 mg. Thus the data can be directly correlated to a 10 to 100 fold improvement in human efficacy. It should be noted that a two-log reduction is the best that can be observed in this model. A 100-fold reduction in *P. aeruginosa* in sputum assays has been correlated with improved pulmonary function (Ramsey et al., 1993). The sustained release of the liposomal/complexed amikacin formulations indicate that a lower dose and/or less frequent dosing can be employed to obtain a greater reduction in bacterial growth than can be obtained with free aminoglycoside.

The efficacy of liposomal/complexed amikacin was studied in a model for chronic pulmonary infection where *P. aeruginosa* was embedded in an agarose bead matrix that was instilled via the trachea of Sprague/Dawley rats. Three days later free amikacin or liposomal/complexed amikacin was dosed every day (FIG. 3) or every other day (FIG. 4) at 1 mg/rat or 10 mg/rat of the given aminoglycoside or 1 mg/rat liposomal/complexed amikacin, as well as with blank liposomes (lipid vehicle) as the control, with five rats per group.

The homogenized rat lungs (frozen) following the 14 day experiment were analyzed for aminoglycoside content and activity. The clinical chemical assay was performed using a TDX instrument while the bioassay was performed by measuring inhibition zones on agar plates embedded with *Bacillus subtilis.*

The results are shown in Table III:

| Formulation | Bioassay (microgram/mL) | Clinical Assay (microgram/mL) |
|---|---|---|
| Lip-An-14 at 10 mg/mL | 9.5 | 9.1 |
| Lip-An-15 at 10 mg/mL | 21.5 | 18.4 |
| Free amikacin at 100 mg/mL | nd | 2.0 |
| Free tobramycin at 100 mg/mL | nd | 1.4 |

Drug weights are for the drug normalized to the absence of any salt form.

The Table III results indicate that aminoglycoside is present and active for both liposomal/complexed antiinfective formulations, while little can be detected for the free aminoglycoside even at the 10-fold higher dose. These further results establish the sustained release characteristics of liposomal/complexed antiinfective, and also confirm that that antiinfective which remains is still active. Of the above formulations only the free tobramycin (0.1 microgram/ml) exhibited any detectable levels of aminoglycoside in the kidneys.

The sustained release and depot effect of liposomal/complexed amikacin is further demonstrated in FIG. 5. Rats were given a chronic pulmonary infection where *P. aeruginosa* was embedded in an agarose bead matrix that was instilled via the trachea, using the same beads employed in the efficacy studies. The rats were then given free tobramycin or liposomal/complexed amikacin (formulation Lip-An-14) via intratracheal administration at the same dose (2 mg/rat). The data, measured in microgram antiinfective per gram lung tissue over time, show that liposomal/complexed antiinfective exhibits a sustained release and depot effect while free tobramycin revealed negligible levels in the lungs by 24 hours, primarily due it is believed to rapid systemic absorption. This greater than a hundred-fold increase of antiinfective in the lung for liposomal/complexed amikacin in an infected rat supports the idea of a sustained release liposomal/complexed antiinfective that can be taken significantly less often than the currently approved TOBI™ formulation.

The pharmacokinetics of amikacin was determined in rats following intratracheal (IT) administration of either free tobramycin or liposomal/complexed amikacin. A dose of 2 mg/rat was administered. The depot effect of liposomal/complexed antiinfective technology is demonstrated in that in comparison to free tobramycin given IT, a greater than a hundred-fold increase in drug for liposomal/complexed amikacin still remains in the infected lungs twenty-four hours following administration. Thus, the therapeutic level of drug is maintained for a longer period of time in the liposomal formulations compared to free tobramycin.

FIG. 7 shows remarkable residence time and accumulation of effective amounts of antiinfective in the lungs, a result that establishes that relatively infrequent dosings can be used. Each dose is 4 hr. by inhalation (in rat, 3 rats per group, as above) of nebulized liposomal amikacin (DPPC/Chol., 1:1) at 15 mg/ml amikacin. Dosing was at either day one; day one, three and five; or day one, two, three, four and five. Rats providing a given data bar were sacrificed after the respective dosing of the data bar. The formulation is made as in the Example.

Similar anti-infectives can be utilized for the treatment of intracellular infections like pulmonary anthrax and tularemia. In pulmonary anthrax the anthrax spores reach the alveoli in an aerosol. The inhaled spores are ingested by pulmonary macrophages in the alveoli and carried to the regional tracheobronchial lymph nodes or mediastinal lymph nodes via the lymphatics (Pile et al., 1998; Gleiser et al., 1968). The macrophage is central in the both the infective pathway and is the major contributor of host self-destruction in systemic (inhalation) anthrax. In addition to its attributes of sustained release and targeting, liposomal/complexed antiinfective technology can enhance cellular uptake and can use alveolar macrophages and lung epithelial cells in drug targeting and delivery. The possession of these characteristics is believed to facilitate the treatment of these intracellular infections, which infections occur in the lungs and are transported by macrophages. More importantly; these characteristics should make the antiinfective more effective in that the liposomal/complexed antiinfective should be phagocytized by the very cells containing the disease. The antiinfective would be released intracellularly in a targeted manner, thereby attacking the infection before it is disseminated. The encapsulated drug can be an already approved pharmaceutical like ciprofloxacin, tetracycline, erthyromycin or amikacin. Liposomal/complexed ciprofloxacin has been developed.

In a study this compound was administered to mice and compared to both free ciprofloxacin administered intratracheally and free ciprofloxacin administered orally, with all three compounds given at the same dose (FIG. 6). The dose for each mouse was 15 mg/kg, with three mice per group. Liposomal/complexed cipro was in DPPC/Cholesterol (9:1), at 3 mg/ml cipro, with the formulation produced as in the Example. The lipid to drug ratio was 12.5:1 by weight. In comparison to orally administered ciprofloxacin, liposomal/complexed ciprofloxacin was present in the mice lungs at amounts over two orders of magnitude higher than free ciprofloxacin. Moreover, only liposomal/complexed ciprofloxacin showed levels of drug in the lung after 24 hours, while the orally administered drug was undetectable in less than two hours. This data supports the use of liposomal/complexed ciprofloxacin and other antiinfectives like aminoglycosides, tetracyclines and macrolides for the treatment and for the prophylactic prevention of intracellular diseases used by bioterrorists.

One type of process of manufacture of liposomal/complexed typically comprises ethanol infusion at room temperature, which is below the phase transition temperature for the lipids used in the formulation. Liposomes in the form of small unilamellar vesicles (SUVs) are mixed with an aqueous or ethanolic solution containing the bioactive agent to be entrapped. Ethanol is infused into this mixture. The mixture immediately forms either extended sheets of lipid or multilamellar vesicles (MLVs). The extended sheets of lipid, if formed, can be induced form MLVs upon removal of ethanol by either sparging or washing by such methods as centrifugation, dialysis or diafiltration. The MLVs will typically range in diameter between approximately 0.1 and approximately 3.0 μm.

Or, the lipids to be employed are dissolved in ethanol to form a lipid-ethanol solution. The lipid-ethanol solution is infused in an aqueous or ethanolic solution containing the molecule of the bioactive agent to be entrapped. All manipulations are performed below the phase transition of the lowest melting lipid. The mixture immediately forms either extended sheets of lipid or multilamellar vesicles (MLVs) (10). The extended sheets of lipid will form MLVs upon removal of ethanol by either sparging or washing by such methods as centrifugation, dialysis or diafiltration. The MLVs will typically range in diameter from approximately 0.1 to approximately 3.0 μm.

| Lipids | Mol ratio | Lipid/amikacin, w/w |
|---|---|---|
| DPPC | — | 1.1 |
| DPPC/DOPG | 9:1 | 1.0 |
| DPPC/DOPG | 7:1 | 3.9 |
| DPPC/DOPG | 1:1 | 2.8 |
| DPPC/DOPG | 1:2 | 2.7 |
| DOPG | — | 2.6 |
| DPPC/Cholesterol | 19:1 | 1.0 |
| DPPC/Cholesterol | 9:1 | 1.2 |
| DPPC/Cholesterol | 4:1 | 1.7 |
| DPPC/Cholesterol | 13:7 | 2.1 |
| DPPC/Cholesterol | 1:1 | 2.7 |
| DPPC/DOPC/Cholesterol | 8.55:1:.45 | 2.0 |
| DPPC/DOPC/Cholesterol | 6.65:1:.35 | 3.0 |
| DPPC/DOPC/Cholesterol | 19:20:1 | 2.5 |
| DPPC/DOPG/Cholesterol | 8.55:1:.45 | 3.8 |
| DPPC/DOPG/Cholesterol | 6.65:1:.35 | 4.1 |
| DPPC/DOPG/Cholesterol | 19:20:1 | 4.2 |
| DPPC/DOPC/DOPG/Cholesterol | 42:4:9:45 | 3.7 |
| DPPC/DOPC/DOPG/Cholesterol | 59:5:6:30 | 3.7 |

A number of formulations with Amikacin were made by the method of the Example, as summarized below:

Further information of forming liposomal/complexed anti-infective can be found in PCT/US03/06847, filed Mar. 5, 2003, which is incorporated herein by reference in its entirety.

EXAMPLE

The following is a detailed description of the manufacture of 150 mL of Liposomal/complexed amikacin.

Total Intial Volume=1.5 L

Ethanol Content=23.5% (v/v)

Lipid Composition: DPPC/Chol (1:1 mole ratio)

Intial [Lipid]=7.6 mg/ml

Intial [amikacin sulfate]=57.3 mg/ml

Final product Volume=150 mL

I) Compounding and Infusion:

7.47 g DPPC and 3.93 g Cholesterol were dissolved directly in 352.5 mL ethanol in a 50 C water bath. 85.95 g amikacin sulfate was dissolved directly in 1147.5 mL PBS buffer. The solution is then titrated with 10N NaOH or KOH to bring the pH to approximately 6.8.

352.5 mL ethanol/lipid was added or infused to the 1147.5 mL amikacin/buffer to give a total intial volume of 1.5 L. The ethanol/lipid was pumped @ 30 mL/min (also called infusion rate) with a peristaltic pump into the amikacin/buffer solution which was being rapidly stirred at 150 RPM in a reaction vessel on a stir plate at room temperature The product was stirred at room temperature for 20-30 minutes.

II) Diafiltration or "Washing" Step:

The mixing vessel was hooked up to a peristaltic pump and diafiltration cartridge. The diafiltration cartridge is a hollow membrane fiber with a molecular weight cut-off of 500 kilodaltons. The product was pumped from the reaction vessel through the diafiltration cartridge and then back into the mixing vessel at room temperature. A back pressure of approximately 7 psi is created throughout the cartridge. Free amikacin and ethanol was forced through the hollow fiber membrane by the back pressure leaving the liposomal amikacin (product) behind. The product was washed 8 times at room temperature. Fresh PBS buffer was added (via another peristaltic pump) to the reaction vessel to compensate for the permeate removal and to keep a constant product volume.

The product was concentrated.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

REFERENCES

1. Veldhuizen, R., Nag, K., Orgeig, S. and Possmayer, F., The Role of Lipids in Pulmonary Surfactant, *Biochim. Biophys. Acta* 1408:90-108 (1998).
2. Hagwood, S., Derrick, M. and Poulain, F., Structure and Properties of Surfactant Protein B, *Biochim. Biophys. Acta* 1408:150-160 (1998).
3. Johansson, J., Structure and Properties of Surfactant ProteinC, *Biochim. Biophys. Acta* 1408:161-172 (1998).
4. Ikegami, M. and Jobe, A. H., Surfactant Protein Metabolism in vivo, *Biochim. Biophys. Acta* 1408:218-225 (1998).
5. Couveur, P., Fattel, E. and Andremont, A., Liposomes and Nanoparticles in the Treatment of Intracellular Bacterial Infections, *Pharm. Res.* 8:1079-1085 (1991).
6. Gonzales-Rothi, R. J., Casace, J., Straub, L., and Schreier, H., Liposomes and Pulmonary Alveolar Macrophages: Functional and Morphologic Interactions, *Exp. Lung Res.* 17:685-705 (1991).
7. Swenson, C. E., Pilkiewicz, F. G., and Cynamon, M. H., Liposomal Aminoglycosides and TLC-65 *Aids Patient Care* 290-296 (December, 1991).
8. Costerton, J. W., Stewart, P. S., and Greenberg, E. P., Bacterial Biofilms: A Common Cause of Persistent Infections, *Science* 284:1318-1322 (1999).
9. Cash, H. A., Woods, D. E., McCullough, W. G., Johanson, J. R., and Bass, J. A., A Rat Model of Chronic Respiratory Infection with *Pseudomonas aeruginosa, American Review of Respiratory Disease* 119:453-459 (1979).
10. Cantin, A. M. and Woods, D. E. Aerosolized Prolastin Suppresses Bacterial Proliferation in a Model of Chronic *Pseudomonas aeruginosa* Lung Infection, *Am. J. Respir. Crit. Care Med.* 160:1130-1135 (1999).
11. Ramsey, B. W., Dorkin, H. L., Eisenberg, J. D., Gibson, R. L., Harwood, I. R., Kravitz, R. M., Efficacy of Aerosolized Tobramycin in Patients with cystic Fibrosis. *New England J. of Med.* 328:1740-1746 (1993).
12. Mendelman, P. M., Smith, A. L., Levy, J., Weber, A., Ramsey, B., Davis, R. L., Aminoglycoside Penetration, Inactivation, and Efficacy in Cystic Fibrosis Sputum, *American Review of Respiratory Disease* 132:761-765 (1985).
13. Price, K. E., DeFuria, M. D., Pursiano, T. A. Amikacin, an aminoglycoside with marked activity against antibiotic-resistant clinical isolates. *J Infect Dis* 134:S249-261 (1976).
14. Damaso, D., Moreno-Lopez, M., Martinez-Beltran, J., Garcia-Iglesias, M. C. Susceptibility of current clinical isolates of *Pseudomonas* aeruginosa and enteric gram-negative bacilli to Amikacin and other aminoglycoside antibiotics. *J Infect Dis* 134:S394-90 (1976).
15. Pile, J. C., Malone, J. D., Eitzen, E. M., Friedlander, A. M., Anthrax as a potential biological warfare agent. Arch. Intern. Med. 158:429-434 (1998).
16. Gleiser, C. A., Berdjis, C. C., Hartman, H. A., & Glouchenour, W. S., Pathology of experimental respiratory anthrax in *Macaca mulatta*. Brit. J. Exp. Path., 44:416-426 (1968).

What is claimed:

1. A method of treating a *Pseudomonas aeruginosa* infection in the lungs of a patient in need thereof, comprising administering to the lungs of the patient an effective amount of a liposomal amikacin formulation, which comprises amikacin and a lipid component, wherein said lipid component consists essentially of a sterol and a phosphatidylcholine, and the lipid and amikacin have a ratio of less than 2.5:1 by weight.

2. The method of claim 1, wherein the patient is a cystic fibrosis patient.

3. The method of claim 1, wherein the phosphatidylcholine is selected from the group consisting of egg phosphatidylcholine (EPC), soy phosphatidylcholine (SPC), hydrogenated egg phosphatidylcholine (HEPC), hydrogenated soy phosphatidylcholine (HSPC), dipalmitoyl phosphatidylcholine (DPPC), dioleoyl phosphatidylcholine (DOPC), dimyristoyl phosphatidylcholine (DMPC), distearoyl phosphatidylcholine (DSPC), palmitoylstearoyl phosphatidylcholine (PSPC), and mixtures thereof.

4. The method of claim 3, wherein the phosphatidylcholine is DPPC.

5. The method of claim 1, wherein the sterol is cholesterol.

6. The method of claim 1, wherein the sterol is cholesterol and the phosphatidylcholine is DPPC.

7. The method of claim 6, wherein the DPPC and cholesterol have a mole ratio of about 19:1, 9:1, 4:1, 13:7or 1:1.

8. The method of claim 7, wherein the DPPC and cholesterol have a mole ratio of about 1:1.

9. The method of claim 1, wherein the administration has a dosing frequency ranging from once a day to once a week during a 14-day treatment period.

10. The method of claim 9 wherein the administration has a dosing frequency of once a day.

11. The method of claim 9 wherein the administration has a dosing frequency of once every two days.

12. The method of claim 9, wherein the administration has a dosing frequency of once every three days.

13. The method of claim 9, wherein the administration has a dosing frequency of once a week.

14. The method of claim 1, wherein the lipid to amikacin ratio is less than 1.1:1 by weight.

15. The method of claim 1, wherein the amikacin is provided as amikacin sulfate.

16. The method of claim 15, wherein the phosphatidylcholine is DPPC.

17. The method of claim 15, wherein the sterol is cholesterol.

18. The method of claim 15, wherein the sterol is cholesterol and the phosphatidylcholine is DPPC.

19. The method of claim 18, wherein the DPPC and cholesterol have a mole ratio of about 19:1, 9:1, 4:1, 13:7or 1:1.

20. The method of claim 18, wherein the DPPC and cholesterol have a mole ratio of about 1.0:1.

21. The method of claim 18, wherein the lipid and amikacin have a ratio of less than 1.1:1 by weight.

22. The method of claim 18, wherein the patient is a cystic fibrosis patient.

23. The method of claim 6, wherein the DPPC and cholesterol have a mole ratio ranging from 19:1 to 1:1.

24. The method of claim 18, wherein the DPPC and cholesterol have a mole ratio ranging from 19:1 to 1:1.

25. A method of treating a *Pseudomonas aeruginosa* infection in the lungs of a patient in need thereof, comprising administering to the lungs of a patient in need thereof an effective amount of a liposomal amikacin formulation, which comprises amikacin and a lipid component, wherein said lipid component consists essentially of cholesterol and dipalmitoylphosphatidylcholine, the lipid and amikacin have a ratio of less than 1.1:1 by weight, and the amikacin is provided as amikacin sulfate.

26. The method of claim 25, wherein the patient is a cystic fibrosis patient.

\* \* \* \* \*